US010835619B1

(12) United States Patent
Morton et al.

(10) Patent No.: US 10,835,619 B1
(45) Date of Patent: Nov. 17, 2020

(54) TARGETED THERAPY TO REPOLARIZE TUMOR-ASSOCIATED MACROPHAGES (TAMS)

(71) Applicant: Verily Life Sciences LLC, Mountain View, CA (US)

(72) Inventors: Stephen Morton, Mountain View, CA (US); Graziella Solinas, Mountain View, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 13 days.

(21) Appl. No.: 15/677,559

(22) Filed: Aug. 15, 2017

Related U.S. Application Data

(60) Provisional application No. 62/377,073, filed on Aug. 19, 2016.

(51) Int. Cl.
*A61K 47/69* (2017.01)
*A61K 38/21* (2006.01)
*A61K 47/68* (2017.01)

(52) U.S. Cl.
CPC ........ *A61K 47/6913* (2017.08); *A61K 38/217* (2013.01); *A61K 47/6851* (2017.08)

(58) Field of Classification Search
None
See application file for complete search history.

(56) References Cited

U.S. PATENT DOCUMENTS

| | | | |
|---|---|---|---|
| 10,583,083 B1* | 3/2020 | Wang | A61K 47/50 |
| 2008/0286198 A1 | 11/2008 | Goetsch et al. | |
| 2009/0175873 A1 | 7/2009 | Liu | |
| 2012/0058177 A1 | 3/2012 | Reisfeld et al. | |
| 2012/0258107 A1* | 10/2012 | Graversen | A61K 51/1027 |
| | | | 424/135.1 |
| 2012/0276193 A1 | 11/2012 | Graversen et al. | |

OTHER PUBLICATIONS

Weagel et al (Journal of Clinical & Cellular Immunology, 2015, 6:4, internet pp. 1-8).*
Fraternale et al (Journal of Clinical & Cellular Immunology, 2015, 6:2, internet pp. 1-10).*
Hofkens et al (PLoS ONE, 2013, 8:e54016, p. 1-11).*
Graversen et al (Membranes, 2015, 5:228-252).*
Kono et al (Cancer Science, 2014, 105:1049-1055).*
Weagel et al (Journal of Clinical & Cellular Immunology, 2015, 6:4).*
Fraternale et al (Journal of Clinical & Cellular Immunology, 2015, 6:2).*
Duluc et al (In J Cancer, 2009, 125:367-373).*
Etzerodt et al (J Controlled Release, 2012, 160:72-80).*
Perche et al (Journal of Drug Delivery, 2013, Article ID 705265, 32 pages).*
Sercombe et al (Frontiers in Pharmacology, 2015, 6:1-13).*
Marques-Gallego et al (BioMed Research International, 2014, article ID 129458, 12 pages).*
Melis Çağdaş, Ali Demir Sezer and Seyda Bucak (Jul. 25, 2014). Liposomes as Potential Drug Carrier Systems for Drug Delivery, Application of Nanotechnology in Drug Delivery, Ali Demir Sezer, IntechOpen, DOI: 10.5772/58459.*
Huang et al (Journal of Controlled Release, 2012, 158:286-292).*
Tang et al Immunology, 2012, 138:93-104).*
Kelly et al (Journal of Drug Delivery, 2011, article ID 727241, 11 pages).*
Akbarzadeh et al., "Liposome: classification, preparation, and applications", Nanoscale research letters 8.1 (2013): 102.
Ashley et al., "Liposomal bortezomib nanoparticles via boronic ester prodrug formulation for improved therapeutic efficacy in vivo", Journal of medicinal chemistry 57.12 (2014): 5282-5292.
Bozzuto et al., "Liposomes as nanomedical devices", International journal of nanomedicine 10 (2015): 975.
Daniel et al., "Dual-responsive nanoparticles release cargo upon exposure to matrix metalloproteinase and reactive oxygen species", Chemical Communications 52.10 (2016): 2126-2128.
Dasgupta et al., "Non inflammatory boronate based glucose-responsive insulin delivery systems", PLoS one 7.1 (2012): e29585.
De Belder et al., "Preparation and properties of fluorescein-labelled hyaluronate", Carbohydrate Research 44.2 (1975): 251-257.
De Palma et al., "Macrophage regulation of tumor responses to anticancer therapies", Cancer cell 23.3 (2013): 277-286.
Etzerodt et al., "CD163 and inflammation: biological, diagnostic, and therapeutic aspects", Antioxidants & redox signaling 18.17 (2013): 2352-2363.
Liu et al., "Legumain protease-activated TAT-liposome cargo for targeting tumours and their microenvironment", Nature communications 5 (2014): 4280.
Moon et al., "Interbilayer-crosslinked multilamellar vesicles as synthetic vaccines for potent humoral and cellular immune responses", Nature materials 10.3 (2011): 243-251.
Olympus , ""Improving Drug Delivery with Macrophage Targeting"", May 16, 2013.
Saravolac et al., "Effect of liposome-encapsulation on immunomodulating and antiviral activities of interferon-γ", Antiviral research 29.2-3 (1996): 199-207.
Zhang et al., "Biocompatible Reactive Oxygen Species (ROS)—Responsive Nanoparticles as Superior Drug Delivery Vehicles", Advanced healthcare materials 4.1 (2015): 69-76.

(Continued)

*Primary Examiner* — Laura B Goddard
(74) *Attorney, Agent, or Firm* — Kilpatrick Townsend & Stockton LLP

(57) ABSTRACT

Provided herein is a tumor associated macrophage (TAM)-targeting liposome. The liposome has a lipid bilayer, a targeting agent associated with the lipid bilayer, and a repolarizing agent associated with the lipid bilayer. The targeting agent optionally comprises an antibody or fragment thereof that selectively binds a TAM, whereas the repolarizing agent repolarizes the TAM upon binding of the TAM by the targeting agent. Also provided is a pharmaceutical composition comprising the TAM-targeting liposomes and a method of treating a subject with cancer with the compositions or liposomes described herein.

11 Claims, 2 Drawing Sheets

(56) References Cited

OTHER PUBLICATIONS

U.S. Appl. No. 15/677,555, "Non-Final Office Action", dated Apr. 29, 2019, 12 pages.
Allavena et al., "Immunology in the Clinic Review Series; Focus on Cancer: Tumour-Associated Macrophages: Undisputed Stars of the Inflammatory Tumour Microenvironment", Clinical and Experimental Immunology, vol. 167, No. 2, Feb. 2012, pp. 195-205.
U.S. Appl. No. 15/677,555, "Final Office Action", dated Sep. 19, 2019, 10 pages.
Sharma et al., "Liposomes as Targeted Drug Delivery Systems in the Treatment of Breast Cancer", Journal of Drug Targeting, vol. 14, No. 5, Jun. 2006, pp. 301-310.
U.S. Appl. No. 15/677,555, "Advisory Action", dated Dec. 5, 2019, 5 pages.
U.S. Appl. No. 15/677,555, "Notice of Allowance", dated May 7, 2020, 8 pages.

* cited by examiner

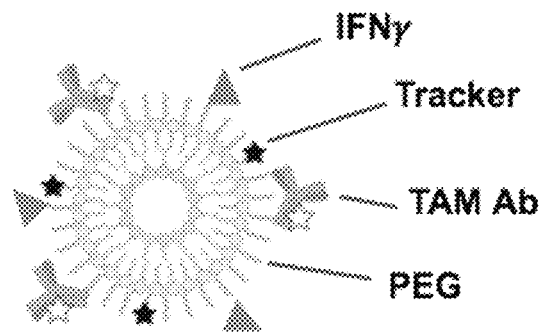
FIG. 1
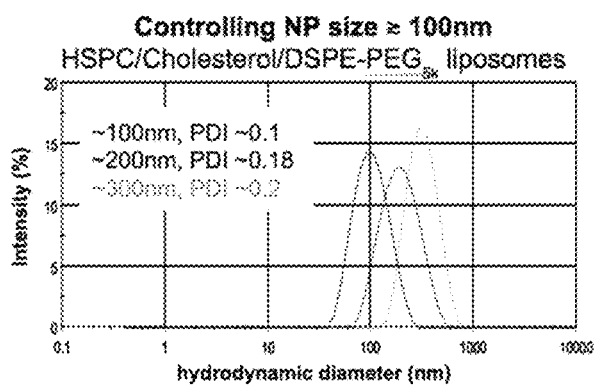 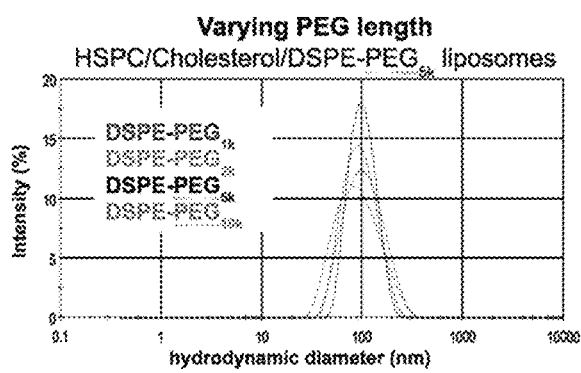
FIG. 2A  FIG. 2B

TARGETED THERAPY TO REPOLARIZE TUMOR-ASSOCIATED MACROPHAGES (TAMS)

CROSS REFERENCE TO RELATED APPLICATION

This application claims priority to U.S. Provisional Application No. 62/377,073, filed Aug. 18, 2016, which is incorporated by reference herein in its entirety.

BACKGROUND

Therapeutic agents in nanoparticles, such as liposomes, may passively reach target organs, tissues, cell, or microenvironments such as tumor microenvironments. Tumor-associated macrophages (TAMs) play a role in tumor growth and metastasis, actively maintaining a immuno-suppressive state in the tumor microenvironment. TAMs also appear to contribute to resistance to various therapeutic agents and to promote tumor cell growth and metastasis.

SUMMARY

Provided herein is a TAM-targeting liposome. The liposome has a lipid bilayer, a targeting agent associated with the lipid bilayer, and a repolarizing agent associated with the lipid bilayer. The targeting agent comprises an antibody or fragment thereof that selectively binds a TAM, whereas the repolarizing agent repolarizes the TAM upon binding of the TAM by the targeting agent. Also provided are a pharmaceutical composition comprising the TAM-targeting liposomes and a method of treating a subject with cancer with the compositions or liposomes described herein.

BRIEF DESCRIPTION OF THE DRAWINGS

FIG. 1 is a schematic showing an exemplary TAM-targeted liposome. The liposome includes a lipid bilayer, a targeting agent (e.g., an antibody (Ab)), and a repolarizing agent. The targeting agent associated with the surface of the liposome specifically targets TAMs. The repolarizing agent repolarizes TAMs upon binding of the TAM by the targeting agent. Shown is a liposome including a single lipid bilayer (unilamellar liposome). The liposome as shown includes polyethylene glycol (PEG) and a tracker (a detectable marker) associated with the outer surface of the lipid bilayer. The exemplary liposome shows the tracker, the repolarizing agent, and the antibody associated with the outer surface of the lipid bilayer and, more particularly, bound to PEG associated with the outer surface of the lipid bilayer.

FIG. 2A is a graph showing the size distribution of liposomes made from hydrogenated soy phosphatidylcholine (HSPC), Cholesterol, and PEGylated distearoyl glycerol phosphoethanolamine (DSPE-PEG5K) and their Polydispersity Index (PDI). FIG. 2B is a graph showing the effect of varying PEG length on size distribution of HSPC:Cholesterol:DSPE-PEG liposomes at a desired size range of 100 nm.

FIG. 3A shows the results of surface incorporation of Fab using dibenzocyclooctyne (DBCO)-azide click chemistry. FIG. 3B shows the results of surface incorporation of Fab using tetrazine trans-cyclooctene (Tz-TCO) click chemistry.

DETAILED DESCRIPTION

Figure 3A:
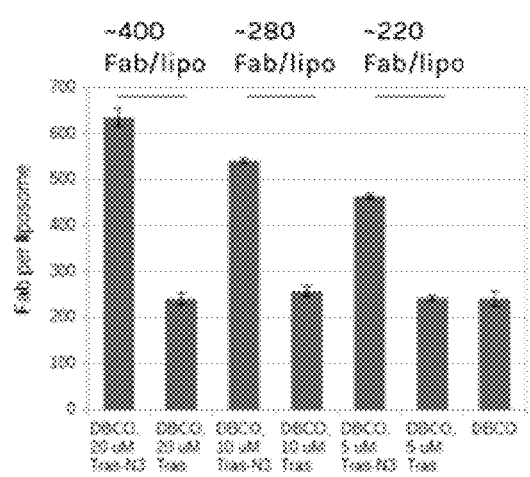
FIGS. 3A and 3B are graphs showing the number of antibody fragments (Fab) per liposome.

Macrophages are capable of shifting phenotypes in response to microenvironmental stimuli. Macrophages are broadly categorized as either classically activated M1 and alternatively activated M2 macrophages. The M1 macrophage is involved in, among other things, antitumor immunity, whereas the M2 macrophage has pro-tumorigenic properties. Tumor-associated macrophages (TAMs), which closely resemble M2-polarized macrophages, accumulate in tumors and this accumulation correlates with a poor clinical outcome. TAMs may express a mixed M1/M2 phenotype but are usually predominately one phenotype or the other. As used herein, the term M2-like TAM refers to a TAM that predominantly exhibits an M2-like phenotype, and the term M1-like TAM refers to a TAM that predominantly exhibits an M1-like phenotype. The phenotype of a TAM or population of TAMs may be determined by a skilled artisan. For instance, an M1-like phenotype is determined by measuring increased expression of pro-inflammatory cytokines, e.g., interleukin (IL)-1β, IL-12, and tumor necrosis factor-α (TNF-α); increased production of reactive oxygen species; or antigen presentation through major histocompatibility complex (MHC) class II molecules as compared to M2-like phenotype. See, e.g., De Palma et al., Cancer Cell, 23:277-286 (2013), which is incorporated herein by reference in its entirety. An M2-like phenotype is determined by measuring increased production of anti-inflammatory cytokines, e.g. IL-10; reduced expression of pro-inflammatory cytokines; increased expression of scavenger receptors, e.g. mannose receptor (MRC1/CD206), and hemoglobin/aptoglobin scavenger receptor (CD163) as compared to M1-like phenotype.

Active targeting of liposomes to TAMs using a targeting moiety reduces degradation of the repolarizing agents contained in or attached to the liposomes and reduces any toxicity burden on the non-targeted parts of the body, thereby maximizing therapeutic effectiveness within the tumor microenvironment. Markers overexpressed on TAMs can be exploited to direct liposomes to the tumor and, more specifically, to the TAMs. Since all tumors are supported by TAMs, TAM-targeted liposomes provide a therapeutic approach for a broad range of cancer types. Thus, provided herein are liposomes that specifically target and repolarize TAMs. The TAM-targeting liposomes include a lipid bilayer, a targeting agent associated with the lipid bilayer, and a repolarizing agent associated with the lipid bilayer. The targeting agent optionally comprises an antibody or fragment thereof that selectively binds a TAM. The repolarizing agent associated with the lipid bilayer repolarizes TAMs from an M2-like phenotype to an M1-like phenoptype at or near the site of a tumor.

As used herein, the term associated with refers to interaction with (e.g., non-covalently), attachment to (e.g., through a covalent linkage) or are otherwise location in proximity to another component. For example, an agent or moiety that is associated with a lipid bilayer may be associated with that lipid bilayer in any number of ways. It may be encapsulated within the lipid bilayer, directly or indirectly (e.g., by a linker molecule(s)) attached to an inner surface of the lipid bilayer, directly or indirectly attached to an outer surface of the lipid bilayer (e.g., by attachment directly to a lipid or to PEG), partially or fully embedded within the lipid bilayer, or any combination thereof.

Liposomes are vesicles comprising one or more bilayers composed of amphipathic molecules, like lipids. When lipids are placed in an aqueous medium, the hydrophilic interaction of the lipid head groups results in the formation of multilamellar or unilamellar vesicles that resemble biological membranes in the form of a spherical shell. Liposomes may be small (0.025-0.05 µm) to large (0.05-10 µm). Optionally, the liposomes described herein have diameters of about 50-5,000 nm or 50-1,000 nm or diameters of less than 5,000 nm or 1,000 nm. Liposomes can be unilamellar (having one lipid bilayer) or multilamellar (having two or more lipid bilayers), and a population of liposomes may contain both unilamellar and multilamellar liposomes. See, e.g., Akbarzadeh et al., *Nanoscale Res. Letters,* 8:102-110 (2013), which is incorporated by reference herein in its entirety. By way of example, a unilamellar liposome may be about 100 nm in diameter. Multilamellar liposomes as described herein optionally include cross-linkages between the lipid bilayers. Such cross-linkages include, by way of example, boronic ester or thioketal cross-linkages.

As used herein, an inner cavity or core is the space inside the innermost lipid bilayer of a liposome, and an interbilayer or interlamellar space is the region between any two lipid bilayers. In a multilamellar liposome having, for example, three lipid bilayers, the inner cavity would be the space within the first (inner-most) lipid bilayer, an interbilayer space would be between the first and second (middle) lipid bilayers, and another interbilayer space would be between the second and third (outer-most) lipid bilayers.

Each bilayer of the liposome has two layers of amphipathic lipids. The hydrophobic portions of the lipids of the layers project toward each other, minimizing their interaction with the surrounding aqueous environments. The hydrophilic portions of the lipids face the opposite way and form an interface with the aqueous environment. Lipids used to prepare liposomal lipid bilayers include, but are not limited to, phospholipids, sphingolipids, glycosphingolipids, saturated glycerides, steroids such as cholesterol, synthetic phospholipids, and any combinations thereof. Optionally, one or more lipids in the lipid bilayer contains a hydroxyl group and/or a diol head group. The lipids of the lipid bilayer can include one or more different types of lipids. Optionally, the lipids comprise hydrogenated soy phosphatidylcholine (HSPC), distearoyl glycerol phosphoethanolamine (DSPE), or a combination thereof. The two or more lipids may be packed together to form a bilayer or certain of the lipids may be integrated into the hydrophobic portion of the bilayer. It should be noted that a lipid bilayer may be continuous or composed of islands of lipid bilayer. It should also be understood that the hydrocarbon chains of any of the various lipids can be of the same, approximately the same, or differing lengths. Optionally one or more of the lipids are PEGylated.

Although liposomal lipid bilayers typically contain lipids as the predominant structural molecule, the bilayers or the lipids themselves may contain one or more additional components. Optionally, the additional components include, but are not limited to, detergents, protein-conjugated molecules, PEG, PEGylated molecules, and molecules with aliphatic anchors. The additional components may be inserted into lipid bilayers by, for instance, hydrophobic interaction, non-covalent attachment to lipid bilayers, or covalent attachment to lipid bilayers by, for instance, bond formation with lipid head groups. The additional components in the liposomal lipid bilayers may alter the properties of the lipid bilayer, including but not limited to, membrane fluidity, permeability, flexibility, fusogenicity, stability, charge/electrostatics, symmetry, cellular uptake, degradation, and the like. By way of example, addition of cholesterol to a lipid bilayer decreases permeability and fluidity of the liposome, whereas PEG increases the duration of circulation. See e.g., Bozzuto et al., *Intl J. of Nanomedicine,* 10: 975-999 (2015), which is incorporated herein by reference in its entirety.

Methods for making liposomes are known. For example, liposomes may be prepared by dissolving lipids in a solvent, which may optionally contain an emulsifier, followed by drying to form a thin lipid film. The lipid film is then hydrated to form sheets of lipid bilayers. Using hydration and agitation or sonication, for example, the lipid bilayers form spherical lipid bilayers. Fusion, extrusion, solvent addition, freeze-thaw, detergent removal, or further agitation may be used, as desired, to control liposome homogeneity in size and lamellarity. For instance, extrusion and sonication can produce unilamellar liposomal vesicles. A liposome including one or more targeting molecules and therapeutic agents (e.g., a repolarizing agent) can be made by a variety of methods. See, e.g., Bozzuto et al., *Intl J. of Nanomedicine,* 10: 975-999 (2015); Akbarzadeh et al., *Nanoscale Res. Letters,* 8:102-110 (2013), which are incorporated herein by reference in their entireties.

The provided liposomes include one or more targeting agents associated with a lipid bilayer, optionally associated with the outer surface of the lipid bilayer of the liposome. In multilamellar liposomes, the one or more targeting agents or moieties are optionally associated with at least the outermost lipid bilayer and optionally on the outer surface of the outermost lipid bilayer. The targeting agent optionally comprises an antibody or fragment thereof that selectively binds a TAM, but other targeting agents (e.g., a receptor ligand or portion thereof) may be used so long as they selectively bind a TAM. Optionally, the targeting agent selectively binds a TAM-specific marker selected from the group consisting of a scavenger receptor, a chemokine receptor, a cytokine receptor, a toll-like receptor, a NOD-like receptor, a RIG-I-like receptor, a C-type lectin receptor, a pattern recognition receptor, an enzyme, or any combination thereof. Optionally, the liposome includes one or more targeting agents that selectively bind CD163 or legumain. Optionally, the liposome includes a targeting agent that binds CD163 and a targeting agent that binds legumain.

Antibodies as used herein for targeting may be recombinant, monoclonal, polyclonal, single chain, chimeric or humanized antibodies. Such antibodies may be intact antibodies or may be any one of a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

Antibodies may be made using a number of different techniques (see, e.g., Kohler and Milstein, Nature 256:495-497 (1975); Kozbor et al., Immunology Today 4: 72 (1983); Cole et al., Monoclonal Antibodies and Cancer Therapy, Alan R. Liss, Inc. (1985), pp. 77-96; Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody may be cloned from a hybridoma and used to produce a recombinant monoclonal antibody. Gene libraries encoding heavy and light chains of monoclonal antibodies also are made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce the targeting antibodies. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg and Huszar, Intern. Rev. Immunol. 13:65-93 (1995)). Alternatively, phage display technology may be used to identify antibodies and heteromeric Fab fragments that specifically bind to the selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies used herein may also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; Verhoyen et al. (1988) Science 239:1534); and Winter and Milstein (1991) Nature 349:293. Generally, a humanized antibody has one or more amino acid residues from a non-human source. Humanization may be performed in a variety of ways. See, e.g., Morrison et al., PNAS USA, 81:6851-6855 (1984); Jones et al., Nature 321:522-525 (1986); Riechmann et al., Nature 332:323-327 (1988); Morrison and Oi, Adv. Immunol., 44:65-92 (1988); Verhoeyen et al., Science 239:1534-1536 (1988); Presta, Curr. Op. Struct. Biol. 2:593-596 (1992); Padlan, Molec. Immun., 28:489-498 (1991); and Padlan, Molec. Immun., 31(3):169-217 (1994)). Such humanized antibodies are chimeric antibodies in which substantially less than an intact human variable domain has been substituted by the corresponding sequence from a non-human species. In practice, humanized antibodies are typically human antibodies in which some or all CDR residues and possibly some framework residues are substituted by residues from analogous sites in rodent antibodies having the desired specificity.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc. or (b) the variable region, or a portion thereof, is altered, replaced or exchanged with a variable region having a different or altered antigen specificity.

Techniques for conjugating agents to antibodies are well known (see, e.g., Freise and Wu, In vivo imaging with antibodies and engineered fragments, Mol. Immunol. pii: S0161-5890(15)00360-0 (2015); Azhdarinia et al., Mol Imaging Biol. Jun; 14(3):261-76 (2012); Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The phrase specifically (or selectively) binds refers to a binding reaction that is determinative of the presence of the bound entity, often in a heterogeneous biologic population. Thus, under designated immunoassay conditions, the antibodies herein specifically bind to a particular protein with at least two times the background level and more typically more than 10 to 100 times background. Specific binding to an antibody under such conditions requires an antibody that is selected for its specificity. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

The targeting agent may be associated with the liposome in one or more ways. It may be directly attached to the lipids of the lipid bilayer, for example, by attachment to a lipid head group. Optionally, the targeting agent is attached to a second component that is part of or associated with the lipid bilayer. The second component can be a lipid, a linker, PEG or other molecule in the lipid bilayer. Thus, by way of example, the targeting agent can be attached to PEG, which is associated with the lipid bilayer. The targeting agent is optionally embedded within the lipid bilayer, attached to an outer surface of the lipid bilayer, or a combination thereof.

As used herein, embedded refers to the insertion of a hydrophobic portion of a molecule into the hydrophobic region of a lipid bilayer such that the inserted molecule is stabilized in the membrane at least partially by hydrophobic interactions. A fully embedded molecule refers to a molecule in which the entire structure of the molecule is embedded within the hydrophobic region of a lipid bilayer. A partially embedded molecule refers to a molecule in which a portion of the molecule is embedded within the hydrophobic region of a lipid bilayer and a portion of the molecule is either embedded in the hydrophilic region of a lipid bilayer (e.g. in the lipid head groups) or protrudes from either surface of the lipid bilayer. By way of example, a targeting agent comprising an antibody or fragment thereof attached to a second component or directly to a lipid in the lipid bilayer is a partially embedded molecule containing a portion embedded within the hydrophobic region of the lipid bilayer and a portion that protrudes from the surface of the lipid bilayer (the antibody or fragment thereof).

The provided liposomes also include one or more repolarizing agents associated with the lipid bilayer. The repolarization agent repolarizes the tumor associated macrophage upon binding of the tumor associated macrophage by the targeting agent. As used herein, repolarize means to convert from predominantly one myeloid activation phenotype to predominantly another myeloid activation phenotype. Repolarization, as used herein, refers to conversion of a TAM or population of TAMS from a predominantly alternatively activated (M2-like) phenotype to a predominantly classically activated (M1-like) phenotype, as M1-like TAMs reduce tumor growth promotion and angiogenesis increase pro-inflammatory responses. Thus, the repolarizing agent converts M2-like TAMs to M1-like TAMs and decreases the ratio of M2-like to M1-like TAMs at or near a tumor. The repolarizing agents are, optionally, anti-tumor or anti-cancer agents that reduce tumor growth and angiogenesis. Suitable repolarizing agent include, but are not limited to, a pro-inflammatory cytokine, a toll-like-receptor agonist, a pattern-recognition receptor agonist, a pro-inflammatory lipid, or any combination thereof. Optionally, the repolarizing agent is the pro-inflammatory cytokine IFN-γ. Optionally, two or more repolarizing agents are included in the liposomes.

Conversion of TAMs from one myeloid activation phenotype to another may be determined by any method known in the art. Optionally, the repolarizing agent elicits an inflammatory response at or near the site of a tumor. An inflammatory response may be determined by any method known in the art. For instance, an inflammatory response may be determined by measuring increased expression of pro-inflammatory markers and cytokines, e.g., C-reactive protein (CRP), IL-1α, IL-1β, IL-2, IL-6, IL-8, IL-12, TNF-α, INF-γ, serum amyloid A, reactive oxygen and nitrogen species (ROS/RNS), or by measuring recruitment of inflammatory mediators, e.g., CD8+ lymphocytes. The repolarizing agent slows or eliminates tumor growth and angiogenesis, which may be measured by any method known in the art.

The repolarizing agent may be associated with the liposome in one or more ways. The repolarizing agent may be encapsulated within the core of a lipid bilayer, attached to an inner surface of a lipid bilayer, embedded within a lipid bilayer, or asscoaited with the outer surface of a lipid bilayer, or any combination thereof. A repolarizing agent encapsulated within the lipid bilayer may be located in the inner cavity or within the interbilayer spaces of the TAM-targeting liposomes. A repolarizing agent may be attached to an inner or outer surface of the lipid bilayer (e.g., covalent attachment to a lipid) or indirectly (e.g., by attachment to a component associated with the lipid bilayer, e.g., PEG).

FIG. 1 depicts an exemplary structural arrangement of a liposome comprising a lipid bilayer, a targeting agent, and a repolarizing agent. As shown in FIG. 1, the lipid bilayer surrounds an inner cavity or core. The targeting agents (e.g., antibodies (Ab)) and repolarizing agent (e.g., IFN-γ) are associated with the lipid bilayer via PEG molecules. The antibody as shown in FIG. 1 is attached to a detectable marker (tracker). Additional detectable markers may be attached to the lipids or PEG molecules, as shown.

The liposomes described herein may include one or more additional active agents. Suitable additional active agents include, but are not limited to, nucleic acids, polypeptide, antibodies (or fragments thereof), small molecules, lipids, carbohydrates, and any combination thereof. The additional active agent or agents may be a therapeutic agent (e.g., a chemotherapeutic agent or phototherapeutic agent), a diagnostic or tracking agent (e.g., a detectable marker), or any combination thereof. The additional active agent or combination of active agents may be associated with the liposome in one or more ways, including the same associations that the targeting and repolarizing agents may have with the liposome.

Detectable marker is meant any detectable label or tag that can be directly associated with (e.g., a fluorescent molecule attached to a polypeptide, such as an antibody (or fragment thereof), a targeting agent, or a lipid) or indirectly (e.g., by way of a spacer, a molecule such as PEG). It should be noted that detection may involve additional steps, such as use of a secondary or tertiary antibody or ligand, which is itself labeled but which binds selectively to the targeting agent, for example. A detectable marker may be visualized with a variety imaging methods. The detectable marker may be a radio-opaque substance, a radiolabel, a fluorescent label, or a magnetic label. The detectable marker is optionally selected from the group consisting of gamma-emitters, beta-emitters, and alpha-emitters, positron-emitters, X-ray-emitters and fluorescence emitters suitable for localization. Suitable fluorescent compounds include fluorescein sodium, fluorescein isothiocyanate, phycoerythrin, and TEXAS RED® sulfonyl chloride (Molecular Probes, Eugene, Oreg.). See, e.g., de Belder and Wik, Preparation and properties of fluorescein-labelled hyaluronate, Carbohydr. Res. 44(2):251-57 (1975). One skilled in the art is able to ascertain how to attach a detectable label and how to visualize a detectable label.

Contact between the repolarizing agent and a TAM may be mediated by selective binding of the targeting agent to the TAM. The repolarizing agent may remain attached to the liposome or, optionally, be released from the liposome in the presence of TAMs selectively bound by the targeting agent. Targeted contact between the repolarizing agent and the TAM aids in preventing and/or reducing the repolarizing agent's systemic effects. Optionally, contact between the repolarizing agent and the TAM converts M2-like TAMs to M1-like TAMs, elicits an inflammatory response at or near the site of a tumor, or a combination thereof.

The liposomes described herein may be PEGylated with at least one type of PEG molecule. PEGylation as used herein refers to the attachment of polyethylene glycol (PEG) molecules to the surface of a liposome. PEG is a polymer of ethylene oxide and has a structure typically expressed as H—(O—CH2-CH2)n-OH. PEGs are commercially available from Sigma Chemical Co. and other companies. PEGylation can impart desirable properties to liposomes, such as increased stability and duration of circulation when administered to a subject.

Optionally, the liposomes include two or more PEGs. The two or more PEGs may have different chemical compositions, lengths, molecular weights, or other properties. PEG molecules may be selected to accommodate a targeting molecule, e.g., to maintain accessibility of the targeting molecule. Optionally, a PEG includes a moiety, e.g., a terminal hydroxyl moiety, to attach additional components, e.g., a targeting molecule, a detectable marker, and the like. A PEG may optionally be a branched PEG molecule.

PEG may be attached to the lipid bilayer in a variety of ways. PEG may be inserted into the lipid bilayer of the liposome, having a hydrophobic moiety in the lipid bilayer, which stabilizes the PEG by hydrophobic interactions. Alternatively, PEG may be covalently attached to the lipid bilayer (e.g., to lipid head groups of the lipids) or to other molecules in the lipid bilayer (e.g., embedded sterols or proteins). Alternatively, PEG may be attached to the liposome via a linker. As used herein, the term linker refers to a molecule that forms a covalent attachment between at least two complex molecules, thereby bridging the complex molecules. Thus, a linker may be positioned between, and covalently attached to, the PEG and the lipid bilayer or targeting agent, for example.

Methods for making liposomes are known. See, e.g., Bozzuto et al., *Intl J. of Nanomedicine,* 10: 975-999 (2015); Akbarzadeh et al., *Nanoscale Res. Letters,* 8:102-110 (2013), which are incorporated herein in their entireties. For example, liposomes may be prepared by dissolving lipids in a solvent, which may optionally contain an emulsifier, followed by drying to form a thin lipid film. The lipid film is then hydrated to form sheets of lipid bilayers. Using hydration and agitation or sonication, for example, the lipid bilayers form spherical lipid bilayers. Fusion, extrusion, solvent addition, freeze-thaw, detergent removal, or further agitation may be used, as desired, to control liposome homogeneity in size and lamellarity.

Additional components of the lipid bilayer or agents to be added to the inner cavity or interlamellar space(s) may be added during formation of the liposomes or added after formation of the liposomes. If, for example, repolarizing agents or other components are added during formation of the liposome, they are added to the nascent liposomes (e.g., to the lipid solution, to the thin lipid film, to the sheet of lipid bilayer, or during hydration or sonication). If, for example, a PEG or other component is added after formation of the liposome, it is added after the lipid bilayers are sealed to form stable liposomes, for example, by attachment to the surface of the liposomes.

Also described herein are pharmaceutical compositions comprising the TAM-targeting liposomes and a pharmaceutically acceptable carrier. Suitable carriers and excipients and their formulations are described in Remington: The Science and Practice of Pharmacy, 22nd Edition, Lloyd V. Allen, Jr., ed., Pharmaceutical Press (2012). By pharmaceutically acceptable carrier is meant a material that is not biologically or otherwise undesirable, i.e., the material is administered to a subject without causing undesirable biological effects and without interacting in a deleterious manner with the other components of the pharmaceutical composition in which it is contained. If administered to a subject, the carrier is optionally selected to minimize degradation of the active ingredient and to minimize adverse side effects in the subject. A pharmaceutical composition generally comprises agents for buffering and preservation in storage and for appropriate delivery, depending on the route of administration.

The compositions for administration will commonly include the TAM-targeting liposomes and a pharmaceutically acceptable carrier, such as an aqueous carrier. A variety of aqueous carriers can be used, e.g., buffered saline and the like. These compositions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agents in these formulations can vary widely and are selected primarily based on fluid volumes, viscosities, body weight and the like in accordance with the particular mode of administration selected and the subject's needs.

Dispersions of the liposomes can also be prepared in glycerol, liquid polyethylene glycols, mixtures thereof, and in oils. Under ordinary conditions of storage and use, these preparations may contain a preservative to prevent the growth of microorganisms.

The liposomes or pharmaceutical compositions containing the liposomes may be delivered via a variety of means. For example, the liposomes can be administered by intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation.

Oral formulations may include excipients such as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. Oral pharmaceutical compositions optionally comprise an inert diluent or assimilable edible carrier, or they may be enclosed in a hard or soft shell gelatin capsule, or they may be compressed into tablets, or they may be incorporated directly with the food of the diet. For oral therapeutic administration, the liposomes may be incorporated with excipients and used in the form of ingestible tablets, buccal tablets, troches, capsules, elixirs, suspensions, syrups, wafers, and the like. Such compositions and preparations should contain at least 0.1% of the repolarizing agent or liposomes. The percentage of the compositions and preparations may, of course, be varied and may conveniently be between about 2 to about 75% of the weight of the unit or between 25-60%. The amount of liposomes and repolarizing agent in such compositions is such that a suitable dosage can be obtained in a subject.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the liposomes in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of highly concentrated solutions for direct injection is also contemplated. DMSO can be used as a solvent for extremely rapid penetration, delivering high concentrations of the active agents to a small area.

The formulations of liposomes can be presented in unit-dose or multi-dose sealed containers, such as ampules and vials. Thus, the composition are optionally in unit dosage form. In such form, the preparation is subdivided into unit doses containing appropriate quantities of the liposome or repolarizing agent. Thus, the compositions may be administered in a variety of unit dosage forms depending upon the method of administration. For example, unit dosage forms suitable for oral administration include, but are not limited to, powder, tablets, pills, capsules, and lozenges.

Compositions can be formulated to provide quick, sustained or delayed release after administration by employing procedures known in the art. Certain carriers may be more preferable depending upon, for instance, the route of administration and concentration of composition being administered. Suitable formulations for use in the provided compositions can be found in Remington: The Science and Practice of Pharmacy, 22nd Edition, Lloyd V. Allen, Jr., ed., Pharmaceutical Press (2012).

The provided compositions including the TAM-targeting liposomes are useful for treating or preventing cancer in a subject. Thus, provided is a method of treating a subject with cancer or preventing cancer in a subject at risk for cancer comprising administering to the subject an effective amount of the TAM-targeting liposomes as described herein. Optionally, a pharmaceutical composition including the TAM-targeting liposomes and a pharmaceutically acceptable excipient is administered to the subject. In the methods of treatment or prevention, the liposomes or compositions comprising liposomes specifically bind to and repolarize TAMs. Administration of the pharmaceutical composition optionally converts M2-like TAMs to M1-like TAMs, reduces tumor growth and angiogenesis, elicits an inflammatory response at or near the site of a tumor, decreases the ratio of M2-like to M1-like TAMs at or near a tumor, or any combination thereof. As used throughout, reduction and decreases refer to a comparison with a control, such as the same subject without treatment or a control subject with cancer but without treatment, and can refer to any measurable reduction or decrease or to a complete elimination.

As used herein, the term cancer refers to all types of cancer, neoplasm, or malignant tumors found in mammals, including carcinomas, sarcomas, germ cell tumors, blastomas whether primary tumors or metastatic tumors. Exemplary cancers include cancer of the brain, breast, cervix, colon, bladder, head and neck, thyroid gland, adrenal gland, pancreas, liver, kidney, lung, ovary, testes, stomach, esophagus, genitourinary tract, prostate, and uterus. Specific examples include non-small cell lung, melanoma, mesothelioma, multiple myeloma, neuroblastoma, rhabdomyosarcoma, malignant pancreatic insulanoma, medulloblastoma, and endometrial cancer.

Compositions comprising the herein disclosed TAM-targeting liposomes can be delivered to a subject in a variety of ways, including intravenously, intramuscularly, subcutaneously, intraperitoneally, inhalation, intubation, topically, orally, local injection, or the like. If the TAM-targeting liposomes are administered in more than one dose, the TAM-targeting liposomes may be administered by the same or by different delivery methods.

Compositions comprising the herein disclosed TAM-targeting liposomes may be delivered to a subject with cancer in a variety of ways, including intravenously, intramuscularly, subcutaneously, intraperitoneally, inhalation, intubation, topically, orally, locally, or the like. If the TAM-targeting liposomes or compositions thereof are administered in more than one dose, the TAM-targeting liposomes or composition may be administered by the same or by different delivery methods for the various doses. The TAM-targeting liposomes or compositions containing the liposomes may be administered locally or systemically. When the liposomes or compositions are administered systemically, the liposomes may circulate and remain intact until the targeting agent binds a TAM. When the targeting agent binds a TAM, the repolarizing agent and, if present, additional active agents, are optionally released at or near the site of a tumor.

As used herein, the term treat refers to any delay in onset or one or more symptoms or clinical signs, reduction in the frequency or severity of symptoms, amelioration of symptoms, improvement in patient comfort or function, decrease in severity of the disease state, etc. The effect of treatment can be compared to an individual or pool of individuals not receiving a given treatment or to the same patient prior to or after cessation of treatment. Treatment includes partial or complete ablation of the disease. The term prevent refers to a decrease in the occurrence of a given disease (e.g., a primary cancer or metastasis). Prevention may be complete (no detectable symptoms) or partial, such that occurrence is delayed or results in fewer symptoms than would occur absent treatment. Prevention optionally occurs before diagnosis or after a determination of a pre-cancerous condition. Prevention optionally refers to after diagnosis where metastasis is prevented.

By effective dose or amount as used herein is meant a dose of liposomes, repolazing agent, or pharmaceutical composition containing the liposoms and repolazing agent that produces the desired effect(s) (i.e., treating or preventing cancer). Determining the dosage and formulation is within the skill of the skilled artisan. See, e.g., Lieberman, Pharmaceutical Dosage Forms (vols. 1-3, 1992); Lloyd, The Art, Science and Technology of Pharmaceutical Compounding (1999); Remington (2012); and Pickar, Dosage Calculations ($9^{th}$ edition) (1999)). An effective dose or amount may ameliorate one or more symptoms or clinical signs of a disease. For example, for a given parameter (e.g., a clinical sign or symptom), an effective amount shows a desired increase or decrease of at least 5%, 10%, 15%, 20%, 25%, 40%, 50%, 60%, 75%, 80%, 90%, or 100%. The efficacy may also be expressed as "-fold" increase or decrease. For example, an effective amount results in at least a desired 1.2-fold, 1.5-fold, 2-fold, 5-fold increase or decrease as compared to a standard control. An effective amount may prevent or delay the onset of a disease or one or more symptoms of a disease.

The exact dose, formulation, and dosing regimen of the TAM-targeting liposomes will depend on a number of factors including the purpose of the treatment, the species of the subject, the age and weight of the subject, the disease to be treated, the severity of the disease, the amount and type of active agent in the liposomes, and the like. Determining the dosage, formulation and dosing regimen is within the skill of one skilled in the art using known techniques. See, e.g., Lieberman, Pharmaceutical Dosage Forms (vols. 1-3, 1992); Lloyd, The Art, Science and Technology of Pharmaceutical Compounding (1999); Remington (2012); and Pickar, Dosage Calculations ($9^{th}$ edition) (1999)). Thus, treatment may include administering a single dose or multiple doses of the TAM-targeting liposomes or compositions thereof. The TAM-targeting liposomes or composition containing the liposomes, as disclosed herein, can be administered to the subject, for example, daily, multiple times daily (e.g., 2, 3, 4, or 6 times daily), weekly, multiple times weekly, monthly, multiple times monthly or any effective regimen. The treatment can be administered alone or in combination with any other treatment modalities or agents. The additional treatment may be administered simultaneously with the first treatment, at a different time, or on an entirely different therapeutic schedule (e.g., the first treatment can be daily, while the additional treatment is weekly). Similarly, the dose may be the same or different with each administration.

In the provided methods of treatment, additional therapeutic agents can be used that are suitable for treating cancer or for treating the side-effects of other therapeutic agents. Thus, the provided methods of treatment optionally further comprise administering one or more additional therapeutic agents to the subject. Suitable additional therapeutic agents include, but are not limited to, analgesics, anesthetics, analeptics, corticosteroids, anticholinergic agents, anticholinesterases, anticonvulsants, antineoplastic agents, allosteric inhibitors, anabolic steroids, psychotherapeutic agents, neural blocking agents, anti-inflammatory agents, antibiotics, antifungals, antihistamines, antimuscarinic agents, antimycobacterial agents, immunological agents, muscarinics, protease inhibitors, anti-angiogenic or vascular-disrupting agents, vitamins, growth factors, and hormones. The choice of agent and dosage can be determined readily by one of skill in the art based on the given disease being treated.

Combinations of agents or compositions can be administered either concomitantly (e.g., included in the liposomes or as a mixture of additional agents with the liposomes), separately but simultaneously (e.g., via separate intravenous lines or by different by simultaneous forms of administration) or sequentially (e.g., one agent or composition is administered first followed by administration of the second agent or composition). Thus, the term combination is used to refer to concomitant, simultaneous or sequential administration of two or more agents or compositions.

Optionally, the liposomes or compositions thereof contain a detectable marker for use in a method of diagnosis or a method of tracking the liposome in vivo. The method comprises administering the a subject an effective amount of the provided liposomes comprising a detectable marker or a composition of such liposomes and visualizing or localizing the marker at the site of the cancer. The method of localization depends on the type of detectable marker selected and includes, by way of example, x-ray, CT scan, MRI, radionuclide scanning, ultrasound, PET scanning, and the like. Furthermore, localization can include biopsy of a tissue and subsequent histological visualization (e.g., by immunohistochemistry).

Also described herein are kits comprising the disclosed TAM-targeting liposomes or pharmaceutical compositions thereof. The kit comprises one or more dosage units of TAM-targeting liposomes or the pharmaceutical composition thereof. Optionally, the kit comprises instructions for use, one or more additional agents, and/or devices for administering the liposomes or composition. Delivery devices include, but are not limited to, syringes, drip bags, patches, and inhalers. The kit may comprise a solution for reconstituting or diluting the liposomes or composition of liposomes. For example, if a disclosed composition is provided in a solid form that is to be reconstituted for parenteral administration, the kit can comprise a sealed container of a suitable solution in which the disclosed composition can be dissolved to form a liposome-containing solution suitable for parenteral administration. Examples of acceptable solutions include, but are not limited to: water sodium chloride solution, Ringer's, dextrose, dextrose and sodium chloride, and lactated Ringer's.

Disclosed are materials, compositions, and components that can be used for, can be used in conjunction with, can be used in preparation for, or are products of the disclosed methods and compositions. These and other materials are disclosed herein, and it is understood that, when combinations, subsets, interactions, groups, etc. of these materials are disclosed, that, while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein are hereby specifically incorporated by reference in their entireties and at least for the material for which they are cited.

The examples below are intended to further illustrate certain aspects of the methods and compositions described herein, and are not intended to limit the scope of the claims.

EXAMPLES

Example 1. Liposome Synthesis

Liposomes were synthesized by dissolving lipids in organic solvent, drying the lipids to produce a lipid film, hydrating the lipid film, and functionalizing the liposomes by surface conjugation of targeting molecules. In one example, heat-treated scintillation vials were first prepared by storing 20 mL scintillation vials in an oven at 230° C. for at least 2 hours prior to film preparation. 12 mg 1,2-dipalmitoyl-sn-glycero-3-phosphoethanolamine (DPPE) [confirm chemical name of DPPE]+/−0.3 mg were added to the vials. 4 mg cholesterol of a 10 mg/mL stock solution in 2:1 (v/v) chloroform:methanol were then added. A fluorescent dye tracker can optionally be incorporated into the liposomes by first conjugating cyanine5.5 (e.g., cyanine5.5-NHS ester; Lumiprobe) to DPPE, and adding 0.4 mg cyanine5.5-conjugated DPPE from a 1 mg/mL stock solution in 2:1 (v/v) chloroform:methanol. 0.5% DPPE-PEG-X conjugate were added, where X is Tz-TCO or DBCO. Or other click chemistry handles such as methyltetrazine, azide, or others can be used. 5 mL of 2:1 (v/v) chloroform:methanol were then added to fully dissolve all lipid components. Optionally, lipid soluble components, for instance, a lipid soluble cytotoxic agent, may be added according to methods known in the art. The lipid solution was dried down to a uniform lipid film in a rotary evaporator. The vial was sealed with perforated parafilm and placed in desiccator for at least 2 hours to remove trace volatile organics.

The lipid film was hydrated by suspension in 5 mL hydration buffer (10 mM HEPES buffer pH 7.4) while sonicating under applied heat. Repolarization agents can be added to the lipid solution. Liposomes were formed by agitating the lipid suspension, for example by sonication, vortexing, or shaking. Small liposomes (e.g., 200 nm or less in diameter) may be prepared by extruding the hot mixture through filters of the desired size. Liposome suspensions were cooled to room temperature and diluted three-fold with phosphate-buffered saline (PBS). Liposomes were then concentrated to approximately 3-4 mL via spin filtration in 30 kDa MWCO filters.

Using this protocol, liposomes can be scalably and reproducibly manufactured with very precise control over size, composition, and surface characteristics (e.g., association of a wide range of targeting agents, including proteins and small molecules). FIG. 2A shows reproducible control over the size (e.g., diameter) of liposomes produced according to the methods described herein. FIG. 2B shows the herein described methods to produce liposomes can be used to vary the liposomal composition (e.g., variable PEG length) without significantly changing the physicochemical characteristics of the resulting liposomes.

Associating a targeting agent (e.g., Ab or Fab) to the TAM-targeting liposome functionalizes the surface of the liposome. A click handle on the targeting agent complementary to a click chemistry present on the liposome is activated according to methods known in the art. For example, a liposome comprising 1,2-distearoyl-sn-glycero-3-phosphoethanolamine-PEG-tetrazine (DSPE-PEG-Tz) is associated with a targeting agent modified specifically or nonspecifically with the complementary trans-cyclooctene (TCO) click handle. 1 µM targeting molecule (e.g., anti-CD163 Ab or anti-legumain Ab) is added to the liposomes, and the click chemistry association is performed according to methods known in the art at room temperature for 16 hours. Unassociated antibodies are removed by passing the liposomes through a size-exclusion chromatograph (SEC) column using Sephacryl 400 resin. Where Cy5.5 tracker is used, eluted liposomal fractions containing high fluorescence are selected for further analysis. Surface-associated repolarization agents may be associated with the liposome by the same or similar mechanisms. For instance, IFN-γ is modified specifically or nonspecifically with a TCO click handle and serves as a complementary binding partner to DSPE-PEG-Tz in the liposomes.

Figure 3B:
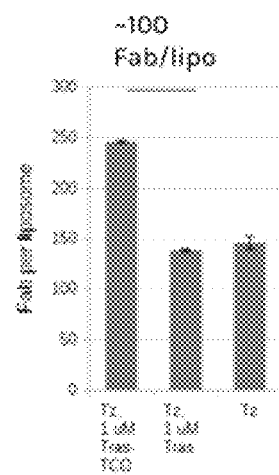

FIG. 3 shows the reproducible association and titration of targeting agents (e.g., Fab for HER2) on the surface of liposomes using two different click chemistries for association (DBCO-azide and Tz-TCO chemistries). The number of targeting agents associated with the TAM-targeting liposomes could be varied according to the conditions for formation of the association.

Example 2. Evaluation of TAM-Targeting Liposome Repolarization Activities In Vitro with Human and Mouse Primary Macrophages TAM-targeted liposome may be evaluated for repolarization activities in vitro using human and/or mouse primary macrophages. Macrophages may be modulated upon liposome phagocytosis. Quantification of macrophage modulation may be performed by gene expression analysis of inflammatory and anti-inflammatory markers, measurement of inflammatory secreted factors, and/or immunofluorescence for surface markers of macrophage polarization. Repolarization activity of TAM-targeting liposomes may be analyzed by exposing cells to TAM-targeting liposomes and determining the polarization status in in vitro differentiated and polarized human macrophages, in tumor-conditioned macrophages (TCMs) generated from tumor cell supernatants, or in co-culture experiments with macrophages and tumor cells.

For co-culture experiments, 40 µL of human macrophages are polarized in 384-well microtiter plates. For unstimulated (M0) macrophages, 10 µL growth medium are added. For M1 polarized macrophages, LPS and IFN-γ are added to final concentrations of 1 ng/mL and 50 ng/mL, respectively, in 50 µL final volumes. For M2 polarized macrophages, dexamethasone and IL-4 were added to final concentrations of 100 nM and 20 ng/mL, respectively, in 50 µL final volumes. The M0, M1 and M2 Macrophages and tumor cells are co-cultured by first thawing and culturing stocks of MDA MB 231 GFP-expressing breast cancer cells (available from Cell Biolabs, Inc., San Diego, Calif.). Cells are harvested and counted on the date of the experiment. For each time point during co-culture, five cell concentrations are used. Cells are serially diluted according to the following: 1:1 (2,500 cells/µL), 1:2 (1250 cells/µL), 1:5 (625 cells/µL), 1:10 (313 cells/µL), and 1:20 (156 cells/µL). Cells are treated with TAM-targeting or control liposomes to determine the polarization status of the Macrophages at each time point.

Example 3. In Vivo Characterization of TAM-Targeting Liposomes

TAM-targeting liposomes may be evaluated in vivo, for instance in rodents, canines, primates, or other mammals. Multiple mouse tumor models may be used to evaluate the anti-tumor activity, pharmacokinetics, biodistribution, and pharmacodynamics of TAM-targeting liposomes as single agents or in combination with checkpoint inhibitors. Tumor models can be selected from models having high infiltration of TAMs (e.g., fibrosarcoma, pancreatic, mammary, ovarian, etc.). Mass cytometry (CyTOF) may analyze modulation of immune cells in blood, spleen, lymph nodes and tumor upon treatment with TAM-targeting liposomes. Changes in secreted factors may be analyzed by biological detection and quantification technologies such as those available from Luminex. Histological staining of biopsied tissue samples can be used to visualize localization of TAM-targeting liposomes in tumor microenvironments and other relevant tissues. In vivo toxicity can be evaluated by a number of methods, such as by maximum tolerated dose (MTD) assays, gross toxicity, hepatic and/or renal function tests, etc. Cross-species variation in biological performance may be evaluated by several methods, such as pharmacokinetic (PK) and/or pharmacodynamic (PD) variations in treatment outcomes, and variations in biodistribution, efficacy, and toxicity profiles.

What is claimed is:
1. A tumor associated macrophage (TAM)-targeting liposome comprising:
   a. a first lipid bilayer, wherein a polyethylene glycol is associated with an outer surface of the first lipid bilayer;
   b. a targeting agent associated with the first lipid bilayer, wherein the targeting agent comprises an antibody or fragment thereof that selectively binds a tumor associated macrophage, wherein the targeting agent selectively binds CD163;
   c. a repolarization agent associated with the first lipid bilayer, wherein the repolarization agent repolarizes the tumor associated macrophage upon binding of the tumor associated macrophage by the targeting agent, wherein the repolarization agent is attached to the outer surface of the first lipid bilayer, wherein the repolarization agent is is interferon gamma (IFN-γ), and wherein the repolarization agent converts M2-like TAM to M1-like TAM;
   d. a detectable marker associated with the targeting agent,
   e. a second lipid bilayer, and f. a cross-linkage between the first lipid bilayer and the second lipid bilayer, wherein the cross-linkage comprises a boronic ester cross-linkage or a thioketal cross-linkage.

2. The TAM-targeting liposome of claim 1, wherein the tumor associated macrophage is an M2-like tumor associated macrophage.

3. The TAM-targeting liposome of claim 1, wherein the liposome further comprises one or more additional active agents.

4. The TAM-targeting liposome of claim 1, wherein the cross-linkage comprises the boronic ester cross-linkage.

5. The TAM-targeting liposome of claim 1, wherein the first lipid bilayer comprises hydrogenated soy phosphatidylcholine (HSPC), distearoyl glycerol phosphoethanolamine (DSPE), or a combination thereof.

6. A pharmaceutical composition comprising the liposome of claim 1 and a pharmaceutically acceptable carrier.

7. The pharmaceutical composition of claim 6, wherein the pharmaceutical composition has pH of 5.5. to 6.5.

8. The pharmaceutical composition of claim 6, wherein the pharmaceutical composition comprises a plurality of liposomes, wherein each liposome of the plurality of liposomes has a diameter of 200 nm or less.

9. A method of treating cancer in a subject comprising administering to the subject the pharmaceutical composition of claim 6 thereby treating the cancer in the subject.

10. The method of claim 9, wherein the subject comprises a tumor and wherein administration of the pharmaceutical composition elicits an inflammatory response at or near the site of the tumor.

11. The method of claim 9, further comprising administering one or more additional therapeutic agents to the subject.

* * * * *